(12) United States Patent
Baumann et al.

(10) Patent No.: US 6,368,851 B1
(45) Date of Patent: Apr. 9, 2002

(54) METHOD AND APPARATUS FOR MEASURING A STATE VARIABLE

(75) Inventors: Werner Baumann, Freiburg; Ralf Ehret, Merdingen; Mirko Lehmann, Freiburg; Günter Igel, Teningen; Hans-Jürgen Gahle, Emmendingen; Bernhard Wolf, Stegen; Ulrich Sieben, Reute; Ingo Freund, Vogtsburg-Oberrotweil; Martin Brischwein, Freiburg, all of (DE)

(73) Assignee: Micronas GmbH, Freiburg (DE)

( * ) Notice: Subject to any disclaimer, the term of this patent is extended or adjusted under 35 U.S.C. 154(b) by 0 days.

(21) Appl. No.: 09/321,458

(22) Filed: May 27, 1999

(30) Foreign Application Priority Data

May 27, 1998 (DE) .......................... 198 23 655
Jun. 23, 1998 (DE) .................... 298 11 066 U

(51) Int. Cl.[7] .............................................. C12M 1/42
(52) U.S. Cl. ............................... 435/285.2; 435/287.2; 435/288.3; 435/288.7; 204/403
(58) Field of Search .................... 435/285.2, 287.2, 435/288.3, 288.7, 173.5, 173.6; 422/82.01, 82.02, 82.05; 204/403, 412, 229.8, 230.2

(56) References Cited

U.S. PATENT DOCUMENTS

| 4,461,304 A | | 7/1984 | Kuperstein | |
| 4,882,281 A | * | 11/1989 | Hilliard et al. | |
| 5,173,158 A | | 12/1992 | Schmukler | 204/182.3 |
| 5,262,128 A | | 11/1993 | Leighton et al. | 422/100 |
| 5,457,041 A | | 10/1995 | Ginaven et al. | 435/172.1 |
| 5,851,489 A | * | 12/1998 | Wolf et al. | 422/82.02 |

FOREIGN PATENT DOCUMENTS

| DE | 38 16 458 A1 | 12/1889 |
| DE | 40 31 138 A2 | 4/1991 |
| DE | 40 04 198 A1 | 8/1991 |
| DE | 44 00 955 A1 | 6/1995 |
| DE | 195 36 384 A1 | 4/1997 |
| DE | 195 36 389 A1 | 4/1997 |
| DE | 44 22 049 C2 | 12/1997 |
| DE | 195 29 371 C2 | 1/1998 |
| DE | 197 12 309 A1 | 5/1998 |
| EP | 0 292 899 A2 | 11/1988 |
| EP | 0 539 660 A2 | 5/1993 |
| EP | 0 585 933 A2 | 3/1994 |
| EP | 0 689 051 A2 | 12/1995 |
| JP | 63-052871 A | 3/1988 |
| WO | WO 97/17426 A | 5/1997 |

* cited by examiner

*Primary Examiner*—David A. Redding
(74) *Attorney, Agent, or Firm*—Akin, Gump, Strauss, Hauer & Feld, L.L.P.

(57) ABSTRACT

A method is provided for measuring a state variable of a biological cell (3) located in a nutrient medium (2) and supported on and adhering to a support area (5). Within the support area (5) for the cell (3) and at a distance from the support area edge, an opening is made in the membrane of the cell (3). The edge of the cell membrane that surrounds the opening and adheres to the support area (5) seals off the liquid found inside the cell (3) from the nutrient medium (2). Through the opening the state variable (2) is measured. An apparatus for performing the method is also provided.

33 Claims, 7 Drawing Sheets

METHOD AND APPARATUS FOR MEASURING A STATE VARIABLE

BACKGROUND OF THE INVENTION

The invention involves a method for measuring at least one state variable of a biological cell located in a nutrient medium, the cell being supported on and adhering to a support area, wherein at least one opening is made in the membrane of the cell for measuring the state variable. The invention further involves an apparatus for measuring at least one state variable of at least one biological cell located in a nutrient medium, the apparatus including an object carrier (specimen slide) having a support area, on which the cell can be supported in an adherent manner, and at least one measuring probe that can be brought into contact with the cell liquid located inside the cell for measuring the state variable, wherein the measuring probe is connected or combined with a measurement amplifier.

From the book, *Human Physiology*, Schmidt; Thews (publisher), $23^{rd}$ edition (1987), pages 20–21, an apparatus of this type is already known, which has a suction device connected to a hollow needle with an inner cavity that has an opening on the open end of the hollow needle. In the inner cavity of the hollow needle, a measuring probe is arranged for measuring the cell potential of the cell. With this device, operating according to the so-called patch-clamp process, the hollow needle is applied on the outside of the cell membrane in order to bring the measuring electrode into contact with the cell liquid by the opening located on the free end of the hollow needle, in order to then generate a partial vacuum in the inner cavity of the hollow needle using the suction device. With this partial vacuum a piece of the cell membrane, located in front of the opening of the hollow needle, is torn out of the membrane structure. Via the resulting opening in the cell membrane, the ions located in the cell liquid get into an electrolyte located in the hollow needle and from there to the measuring probe. A reference electrode functions for determining a reference potential.

The previously known method and associated apparatus have the disadvantage that, for positioning of the hollow needle on the cell, a micromanipulator is necessary. This results in a comparatively complicated and expensive device. Moreover, the accessibility of the cells located on the specimen slide is greatly restricted by the micromanipulator. The process and apparatus are thus suitable only for an investigation of individual, or at most for a simultaneous investigation of a small number of, cells located on the specimen slide.

From U.S. Pat. No. 4,461,304 an apparatus is further known, which has a needle-shaped tip for making an opening in a cell membrane. On the tip a plurality of sensors is arranged for neurophysiological investigations. Even with this device, for positioning of the tip on the cell, a micromanipulator is necessary.

From published European and German patent applications EP 0 689 051 A2; DE 197 12 309 A1; and EP 0 585 933 A2 and German patent DE 195 29 371 C2, apparatus are already known for measuring a cell potential, which have a specimen slide having a plurality of microelectrodes arranged in matrix form, which can be brought into connection with the outside of the membrane of a cell to be investigated. These devices make possible, however, only an extracellular measurement of the cell potential, since no opening is made in the cell membrane.

From published German patent applications DE 195 36 389 A1 and DE 195 36 384 A1 methods are already known for measuring a state variable, in which a biological component is contacted. Also with this method, an opening is not made in the biological component.

In German published patent application DE 38 16 458 A1 a microelectrode is further described, which can be used for a potentiometric or amperometric measurement in the biochemical and medical fields.

German patent DE 44 22 049 C2 discloses an ultra-microelectrode array for chemical and biochemical analyses, which has several pyramids or cone-shaped electrode tips on a substrate. According to statements of the patent document, the ultra-microelectrode array can be inserted into electrode structures for the measurement of oxygen according to Clark.

From U.S. Pat. No. 5,173,158, moreover, a process outside of the generic concept is known for generating new cells, in which cells of a first type located in a liquid are supported by a partial vacuum or hydrostatic pressure on a support area of a porous layer, such that the cells engage with a component in the pores of the porous layer. The porous layer with the cells is arranged between electrode plates bordering on the liquid to which an electric voltage is applied, which opens the cell membrane of the cells in the component that engages with the pores. Thereafter, cells of a second type are brought into the insides of the cells of the first type through these openings.

SUMMARY OF THE INVENTION

Thus, an object of the present invention is to create a method and apparatus of the type mentioned at the outset, which makes possible a simple measurement of a state variable of the cells. In particular, a costly manual positioning of a hollow needle on the cells to be investigated should be avoided.

This object is achieved with respect to the method in that the opening in the cell membrane is made within the support area of the cell and spaced from the support edge, and through this opening the state variable is measured.

In this way it is possible to arrange a poration agent or a poration tool, which is used for making the cell membrane opening, in the support area of the cells on the specimen slide so that the cell is also positioned simultaneously on the poration agent or poration tool when it is supported on the support area. In this way, a costly manual positioning of a poration tool can be omitted. Since the opening is formed in the cell membrane within the support area of the cells and at a distance from the edge of the support area, the membrane area of the cells, which surrounds the opening and is adheringly attached to the support area, seals off the opening from the nutrient liquid. The cell liquid located inside the cell is thus electrically insulated to the greatest extent possible from nutrient liquid. The measured state variable of the cells can, for example, be an ion concentration, a gas quantity, a temperature or any other desired physical, chemical or biological characteristic of a cell.

In order to measure the cell potential of the cells, the electrical voltage between the cell liquid and the nutrient medium can be measured through the opening formed in the cell membrane. Using this process, for example, electrical signals transmitted between nerve cells can be tested. Using this process, electric d.c. and/or a.c. voltage potentials, especially potentials that change quickly in time, can be measured.

In an especially advantageous embodiment of the invention, the opening can be made using electroporation of the cell membrane. For the performance of the process, for example, an electroporation-electrode can be arranged in the support area for the cell, on which the cell is supported in an adherent manner. In order to form the opening in the cell membrane, an electric voltage then only needs to be applied between the electroporation electrode and the nutrient medium, which causes an electrical current flow that opens the cell membrane. After switching off the electroporation voltage, the electric potential can be measured through the opening of the cell membrane between the cell liquid and the nutrient medium. For this purpose, optionally, the electrode used for electroporation can also be used to measure the cell potential, so that the electrode performs a double function.

In another embodiment of the invention, at least one mechanical impulse is applied in order to form the opening in the cell membrane on a portion of the cell membrane. In this process, this portion of the cell membrane detaches from the membrane structure. Optionally, an impulse sequence can also be applied with several individual impulses.

It is especially advantageous when the opening is made in the cell membrane using ultrasound. In this process, it is even possible that the ultrasound is focused on the area of the cell membrane to be opened and/or that several ultrasonic waves are superimposed so that their oscillations are superimposed in the area of the cell membrane to be opened, to produce an oscillation having an increased amplitude. The cell membrane can be opened in this way without contact.

A contact-free opening of the cell membrane can, however, also occur in a manner such that a portion of the cell membrane is irradiated with a high-energy radiation, especially with laser radiation. In this process, the wavelength of the radiation is preferably selected such that the cell membrane absorbs the radiation well. Functionally, the radiation is coupled into the cell in the support area of the cell. Optionally, a laser beam can, however, also be coupled into the cell outside the support area, where in a membrane area located there a small coupling opening is first made, through which the laser beam is then projected through the inside of the cell onto a membrane area located in the support area of the cell, in order to cut out a portion of the membrane from the membrane structure by sweeping of the laser beam around the coupling opening.

In another embodiment of the process, the opening is made by the action of a chemical substance in the cell membrane. As a poration agent, for example, a Perforin or Triton® can be used.

It is especially advantageous if an electric and/or chemical substance and/or a substance that can be activated by radiation is used and if this substance is activated in order to make the opening in the cell membrane by the action of radiation and/or an electric field. The substance is thus activated by the supply of energy. In this process, for example, free radicals are generated, which destroy the portion of the cell membrane that is to be opened. In the inactive condition, the substance acts, for the most part, neutrally relative the cell, so that it has practically no influence on the support of the cell on the support area. A chemical substance can also be used which is chemically activated by the addition of another substance.

Another embodiment of the process provides that a portion of the cell membrane to be opened is disengaged from the membrane structure by impingement with a partial pressure and/or an excess pressure. In this process, for example, in a specimen slide that has the support area, a small opening can be provided within the support area, through which the cell is suctioned to such an extent that the membrane area located in front of the opening is torn out of the membrane structure. In order to open the cell membrane, action can be made through the opening, but also, however, an excess pressure pulse can be exerted on a membrane area of the cell.

It is advantageous that the cell be fixed on the support area by a suction force. In this way, the adhering of the cell on the support area of a specimen slide is improved. The suction force is measured selected such that the cell membrane is not mechanically damaged by the suction force.

It is advantageous when, after making the opening in the cell membrane, cell liquid is removed from the cell through the opening and examined. In this way, it is possible to detect additional cell quantities that are only measured with difficulty inside the cell. Thus, additional information about the physiology of the cell can be obtained.

It is especially advantageous when, after making the opening in the cell membrane, an intracellular manipulation can be performed through the opening, in particular, a medicine and/or a foreign substance and/or a biological substance is brought into the interior of the cell. The effects of the intracellular manipulation can then be observed by measuring a state variable of the cell. Optionally, the intracellular manipulation can also be performed, however, without a state variable of the cell being measured through the opening.

In regards to the apparatus, the previously mentioned purpose is achieved in that the measuring probe and an electric insulator surrounding it are arranged within the support area, such that the cell can be supported on the insulator to seal it from the nutrient medium, and that to open the membrane of the cell, at least one poration tool is arranged in the support area in the area of the measuring probe.

Since the poration tool is arranged within the support area, the cell can automatically be supported on the poration tool located in the support area. In an advantageous way, a costly manual positioning of the poration tool on the cell can thus be omitted. Also, auxiliary devices, such as micromanipulators, are not necessary. In this way it is possible to measure cell quantities at the same time on several cells that are arranged in close proximity to one another. After making the opening in the cell membrane, the edge of the cell membrane surrounding the opening stays in contact with the electric insulator and seals off the opening from the nutrient medium. In this way, the cell liquid located inside the cell is electrically well-insulated from the nutrient medium, so that the cell quantity can be measured through the opening of the cell membrane.

It is advantageous when the poration tool is arranged substantially concentrically around the measuring probe. The measuring probe can then come into good contact with the cell liquid located inside of the after the opening is made in the cell membrane.

In an embodiment which is provided for measuring the potential of the cell, the measuring probe is a measuring electrode, to which is allocated at least one reference electrode that can be brought into contact with the nutrient medium. With a device of this type, the difference in potential between the cell liquid and the nutrient medium can be measured in a simple way.

It is especially advantageous when the measurement electrode also is an electroporation electrode which can be connected to an electric voltage source for the electroporation of cell membrane, and when the electroporation electrode has at least one active electrode area that is arranged within the support area and which is surrounded by the electric insulator. The measuring electrode is thus simultaneously also the poration tool, and fulfills a double function, such that a device results that is constructed in an especially simply manner. The electrode connected to the measurement amplifier can, for example, be applied briefly at the potential of the voltage source using an electronic switch. Optionally, a change-over switch can also be provided, by which the measuring electrode can be selectively connected one after the other to the measurement amplifier or the voltage source. The measuring and electroporation electrode is arranged within the support area of the specimen slide so that a cell supported so as to adhere to the insulator can also optionally be supported on the active electrode area of the electrode or at least approach it until reaching the active area of an electric field that extends from the electrode. When the electroporation voltage is applied to the electrode, an electric current flows which makes an opening in the cell membrane. In the process, the edge of the cell membrane surrounding the opening stays in contact with the electric insulator and seals off the opening from the nutrient medium. The insulator resistance is independent of the cell type and is preferably larger than 10 megaohms. An offset of the potential between the nutrient medium and the cell liquid is thereby for the most part stopped. After the creation of the opening in the cell membrane, the measuring electrode is separated from the electroporation voltage source, so that then the cell potential is applied on the measuring electrode that is in contact with the cell liquid and can be measured with the measurement amplifier. The device has a simple construction and makes possible, for the most part, an automated cell potential measurement.

In an advantageous embodiment of the invention it is provided that the poration tool is an electroporation electrode that is set off at a distance from the measuring probe. The electrode can be connected to an electric voltage source for the electroporation of the cell membrane. The electroporation electrode has at least one active electrode area arranged within the support area and surrounded by the electric insulator. The electroporation electrode is thus separated from the measuring probe. In this way, the effect of the capacitance of the supply lines from the voltage source to the electroporation electrode is reduced to the measurement signal determined by the measuring probe. Thus, changes of the cell potential that are rapid in time, as occurs in nerve cells for example, can be measured even better.

In an especially advantageous further embodiment of the invention, it is provided that the active electrode area of the electroporation electrode has at least one sharp tip or edge and is preferably arranged to project beyond the surface plane of the support area. The active electrode area can thus contact the cell membrane of a cell supported on the support area on the outside. In this way, a good electrical contact between the electrode and the cell membrane is possible. The projecting active electrode area additionally allows a good electrical contact with the cell liquid located inside the cell through the opening of the cell membrane and, above and beyond that, acts to oppose a closing, through cell repair mechanisms, of the opening made by electroporosis in the cell membrane.

It is advantageous if the electroporation electrode is constructed as a hollow electrode which has an inner cavity with an opening located on the surface of the support area, and if the measuring electrode is a rod electrode arranged in the inner cavity of the electroporation electrode, the free end of the rod electrode preferably extending up to the opening of the inner cavity. Inside the hollow electrode, an electrolyte can be arranged which can correspond, for example, to the nutrient medium, so that after the opening of the cell wall, charged particles, especially ions, contained in the cell liquid can migrate through this electrolyte to the electrode. Thus, a larger electrode surface can come into contact with the charged particles. The electric contact between the measuring electrode and the cell liquid is improved by this.

It is especially advantageous when immediately adjacent to the electroporation-electrode a switching component, in particular a static switch, is arranged with which the electroporation electrode can be connected to the electroporation voltage source. The connection line between the electroporation electrode and the electroporation voltage source can then be uninterrupted closely adjacent to the electrode, so that the parasitic capacitance of this connection line is uncoupled from the measuring probe during the measurement of the cell potential. In this way, cell potential voltages that change quickly in time can be measured more exactly. Preferably, the static switch is a low-noise junction-field effect-transistor.

In an advantageous embodiment of the apparatus, the poration tool for opening the cell membrane can be moved using at least one actuator, in particular a piezo element, across the surface of the support area relative to the specimen slide. With this device, the opening is thus made mechanically in the cell membrane. In the process, the poration tool can even be alternately moved away from and toward the cell membrane. For this purpose, the actuator can be connected with a drive device for generating an ultrasonic oscillation. The poration tool can be alternately moved relative to the specimen slide in a direction that runs perpendicular or in a direction that is oblique to the surface of the support area.

It is advantageous when the poration tool has at least one sharp tip or edge that can be brought into contact with the membrane of the cell. The cell membrane can then be better opened by moving the poration tool.

It is especially advantageous when the measuring probe is at the same time also the poration tool and for this can be moved, using the actuator or piezo element, across the surface of the support area relative to the specimen slide. The measuring probe then fulfills a double function, such that an additional poration tool can be omitted.

In another advantageous embodiment, the specimen slide has an optical window in the area of the measuring probe, which is arranged in the beam path of a laser beam in order to open the cell membrane. Using this device, a portion of the cell membrane can be irradiated briefly with high-energy optical radiation, where this area is heated to such an extent, that an opening is made in the cell membrane.

It is especially advantageous when, in order to generate the laser beam, a laser diode is integrated into the specimen slide. In this process, the laser diode can even be arranged directly behind the opening, so that the laser beam can be coupled directly and thus, for the most part, free of losses into the cell membrane supported on the support area.

Functionally, the measuring probe is arranged substantially concentrically around the optical window. The measuring probe can then come into better contact with the cell liquid after opening the cell membrane.

In an advantageous embodiment is provided that the poration tool has, in order to open the cell membrane, a chemical substance and/or at least one outlet opening connected to the supply channel for a chemical substance. The opening can thus also be made in the cell membrane chemically, where as a poration agent, for example, Perforin or Triton® can be used.

In another embodiment the poration tool has at least one channel that opens into the support area, by the use of which a portion of the cell membrane can be impinged in order to make the opening in the cell membrane with a partial vacuum and/or excess pressure. In a device of this type, the opening is thus made in the cell membrane using a partial vacuum or excess pressure, where the partial vacuum or excess pressure is switched off after the opening of the cell membrane. During an opening of the cell membrane by partial vacuum, a suction of the cell liquid out of the inside of the cell is prevented to the greatest extent possible. Correspondingly, during opening of the cell membrane using excess pressure, it is prevented that a medium located in the channel, that is preferably a fluid, can enter into the inside of the cell. In order to switch off the partial vacuum or excess pressure, for example a pressure change occurring during the opening of the cell membrane in the channel can be determined. The partial vacuum or excess pressure can be generated using a suitable auxiliary device, for example a pump, or hydrostatically. In an advantageous way, the channel can also be used prior to supporting the cell, in order to suction off nutrient medium from the support area, so that a current occurs in the nutrient medium, which conducts the cells located therein to the opening of the channel arranged in the area of the measurement electrode.

It is especially advantageous when the measuring probe is constructed as a hollow sensor that is installed into the surface of the specimen slide, and has at least one inner cavity, wherein the inner cavity has an opening on the surface of the support area. In the inside of the hollow electrode, an electrolyte can be arranged, so that charged particles contained in the cell liquid can migrate through the electrolyte to the measuring probe. Thus, a larger surface of the measuring probe can come contact with the charged particles, which improves the electrical contact between the measuring electrode and the cell liquid.

An advantageous embodiment provides that the electric insulator within the support area has a projection that projects beyond the surface plane of the support area, and that the measuring probe is arranged on the free end of the projection, which faces away from the surface of the support area. In this way, a good electrical and/or mechanical contact results between the measuring probe and the cell membrane.

Functionally, it is provided that the cross-section of the projection proceeding out from the surface plane of the support area tapers to the point that projects furthest out. The cell then adheres better with its membrane to the projection of the electric insulator. In addition, the insulator can, in production engineering in the manufacture of the specimen slide, be better applied as a coating on the area of the projection that tapers.

In an advantageous further embodiment of the invention, it is provided that the specimen slide has a profile in the support area, which has at least one profile recess and/or a profile projection that surrounds the measuring probe. In this way, a better seal of the cell liquid is achieved against the nutrient medium by the cell membrane that adheres to the insulator.

It is advantageous when the profile recess and/or profile projection is interrupted in the extension direction by at least one gap. The cell can then better adhere to the surface of the specimen slide in the area of the profile. The profile projection or profile recess can, for example, have a web structure or a structure in the manner of a checkerboard pattern.

It is especially advantageous if the profile recess and/or the profile projection is constructed in a ring-shape, and if preferably several such ring-shaped profile recesses and/or profile projections are arranged essentially concentrically to the measuring probe. Thus, radially to the measuring probe, several profile recesses and/or projections are connected behind each other or interlaced within each other, so that the cell liquid is even better sealed off from the nutrient medium.

A preferred embodiment of the invention provides that the insulator is an insulation layer arranged on the surface of the profile. In an advantageous manner, the path for a leak current flowing on the surface of the insulator from the cell liquid to the nutrient medium is enlarged by the insulation layer profiled in this way, so that the measuring probe or the measuring electrode is insulated even better from the nutrient medium.

Another embodiment provides that the profile projection(s) is (are) mounted on the surface of the insulator. The specimen slide can then be manufactured in a more simple way by production engineering.

It is especially advantageous when in the support area of the specimen slide on its surface, at least one coating that has a cell adhesion protein and/or a hydrophilic coating is arranged. The cell membrane then adheres better to the specimen slide. The cell adhesion coating can for example have laminin, fibronectin, or poly-L-lysine. Possibly, a hydrophobic coating can also be arranged on the edge of the support area that borders the electrode, with bonding positions for the hydrophobic lipids located in the cell membrane.

It is advantageous when as a mechanical guide for the cells, boundary walls are arranged on both sides of the measuring probe, which preferably delimit a groove-like guide channel. In this manner, the measuring electrode(s) is (are) preferably arranged in the middle between the boundary walls at the base of the groove of the guide channel, so that cells located in the guide channel can move essentially only in the extension direction of the guide channel and then inevitably come into contact with the measuring probe.

In an especially advantageous further embodiment of the invention, a field-effect transistor (FET), in particular a junction-field-effect transistor (J-FET) is arranged adjacent to the measuring probe, and the measuring probe is connected for the impedance transformation of the measuring signal to the gate of the FET. In the process, the coupling of the measuring electrode onto the gate is done capacitively in a metal oxide-field effect transistor (MOS-FET), wherein the measuring electrode is preferably arranged directly above the gate of the MOS-FET that is installed into the surface of the specimen slide. In an advantageous way, a junction-FET makes possible a high-ohmic, but nevertheless, low-noise coupling of an intracellular electrical signal. The low input capacitance of the junction-FET allows, in particular, even for rapid changes in the cell potential, obtaining a measuring signal that is, for the most part, free from feedback. By the impedance conversion directly at the measuring site, the screening cost for the connection lines from the measuring electrode to a measurement amplifier and/or an evaluation device can be reduced. The field effect transistors manufactured by the manufacturing processes known in semiconductor technology allow, beyond that, a high integration density.

It is advantageous when at least one liquid channel opens in the support area of the specimen slide, adjacent to the measuring probe, preferably in an area surrounded by this. Through this liquid channel, after the opening of the cell membrane, a small quantity of cell liquid can be suctioned off and/or a biological substance, for example a gene, and/or a foreign substance, a medication or the like, whose effect on the cell is to be investigated, can be added to the cell liquid. To add a substance, the device can optionally also be used without a measuring probe.

Expediently, in the course of the liquid channel, a micropump preferably integrated in the specimen slide is arranged. Optionally, several micropumps can even be allocated to one liquid channel which, for example, can respectively be connected to a cavity located in the specimen slide to support a liquid or a medium that is to be cytologically tested.

It is especially advantageous when within the liquid channel, preferably in a wall of the liquid channel, at least one microsensor is arranged for measuring a quantity of the cell. In this way, additional intracellular parameters, such as ion concentrations, gas contents, enzyme and/or protein concentrations, can be determined.

It is advantageous when, in order to generate an electric field that conducts the cell to the measuring probe, at least one additional electrode is arranged in the support area and/or adjacent to it. An electric field can thereby be generated on the surface of the specimen slide, which exerts a force on the biological cells, whose dielectric constants are distinguished from those of the nutrient medium in which they are arranged. This force guides the cells to the measuring probe.

An especially advantageous further embodiment of the invention provides that in the support area several measuring probes and electroporation electrodes are preferably arranged as an array, and that to each of these measuring probes at least one poration tool is allocated. Such a device allows a locationally triggered measurement of the cell potential on a cell population. In this process, the cell potential can be measured on many cells that are close to each other at the same time. In this way, it is possible, for example, to perform quasi static cell membrane potential measurements on nerve or tumor cells, in order to monitor their electric activity. In this way, it is even possible to monitor the information transfer between the cells, through the locationally triggered and time-triggered measurement of the cell potential, in a cell composite with nerve cells connected through synapses. Optionally, a multiplexer can also be integrated into the specimen slide, by which several measurement and/or electroporation electrodes can be connected alternatingly one after the other with a measurement signal guide, such that the number of the supply lines to the specimen slide constructed as a sensor chip is correspondingly reduced.

BRIEF DESCRIPTION OF THE SEVERAL VIEWS OF THE DRAWINGS

The foregoing summary, as well as the following detailed description of the invention, will be better understood when read in conjunction with the appended drawings. For the purpose of illustrating the invention, there are shown in the drawings embodiment(s) which are presently preferred. It should be understood, however, that the invention is not limited to the precise arrangements and instrumentalities shown. In the drawings, which are schematically drawn.

DETAILED DESCRIPTION OF THE INVENTION

Figure 1:
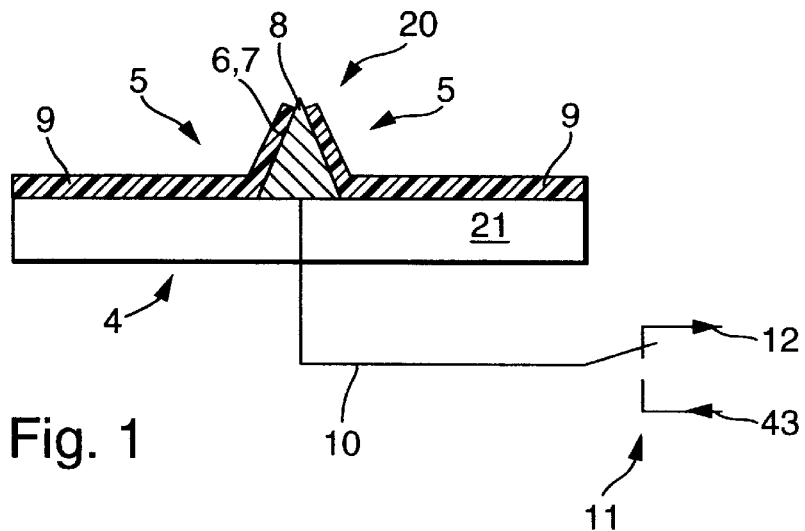
FIG. 1 is a longitudinal section through a measuring and electroporation electrode arranged in the support area of a specimen slide and selectively connectable with a voltage source and a measuring amplifier using a change-over switch.
Figure 2:
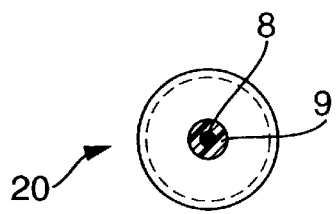
FIG. 2 is a plan view of the measuring electrode according to FIG. 1.

An apparatus, indicated as a whole by 1 for measuring the cell potential of a biological cell 3 (shown in FIG. 11, but for sake of clarity, not shown in the other figures) located in a nutrient medium 2, has a specimen slide 4 that has a support area 5, on which the cell 3 can be supported in an adherent manner. The cell 3 is thus immobilized on the specimen slide 4 and adheres to the support area 5. In the embodiments according to FIGS. 1 and 2 as well as 5 to 17, the specimen slide 4 has within the support area 5 a measuring and electroporation electrode 6,7, which has an active electrode area 8 that projects beyond the surface plane of the support area 5. In the support area 5, an electric insulator 9 is arranged surrounding the active electrode area 8, on which insulator the cell 3 can be mounted to seal off the nutrient medium 2.

In the embodiments according to FIGS. 1, 5, 7 and 11, the electrode can be connected via a conductor path 10 integrated in the specimen slide to a change-over switch 11 with which it can be selectively connected to a measurement amplifier 12 and an electroporation voltage source 43. In order to measure the cell potential, the electrode 6,7 is first brought into contact with the cell liquid located inside the cell 3. To do this, an electric voltage is applied between the electrode 6,7 and the nutrient medium 2, wherein the electrode 6,7 is connected via the change-over switch 11 to the electroporation voltage source 43. An electric current thus flows over the electrode 6,7 into the cell membrane, whereby in the area of the electrode 6,7 an opening is made in the cell membrane, and the active electrode area 8 penetrates through this opening into the cell 3. The electrode 6,7 thereby comes into contact with the cell liquid.

After making the opening in the cell membrane, the electrode 6,7 is connected with the input of the measurement amplifier 12. The outlet of the measurement amplifier 12 is connected with a connection contact 13. An additional connection contact 14 is connected to a reference electrode 15, which is in electrically conducting contact with the nutrient medium 2. Between the connection contacts 13 and 14 an electric voltage arises, which is a measure of the cell potential of the cell 3. Onto the connection contacts 13 and 14 can be connected, for example, a display and evaluation device . The opening made in the cell 3 using the electroporation electrode 6,7 is sealed off from the nutrient medium 2 by the cell membrane area surrounding the opening, where it adheres on the specimen slide 4. A potential equalization between the potential of the electrode 6,7 and the nutrient medium 2 is thereby prevented.

In the embodiments according to FIGS. 1, 9 to 11 and 13, the electrode 6,7 is constructed in an approximately cone shape, wherein the active electrode area 8 projecting beyond the surface plane of the support area is arranged on the tip of the cone and is constructed as a sharp tip. During the application of an electroporation voltage on the electrode 6,7, a particularly high electric field strength thereby arises in the active electrode area 8.

Figure 5:
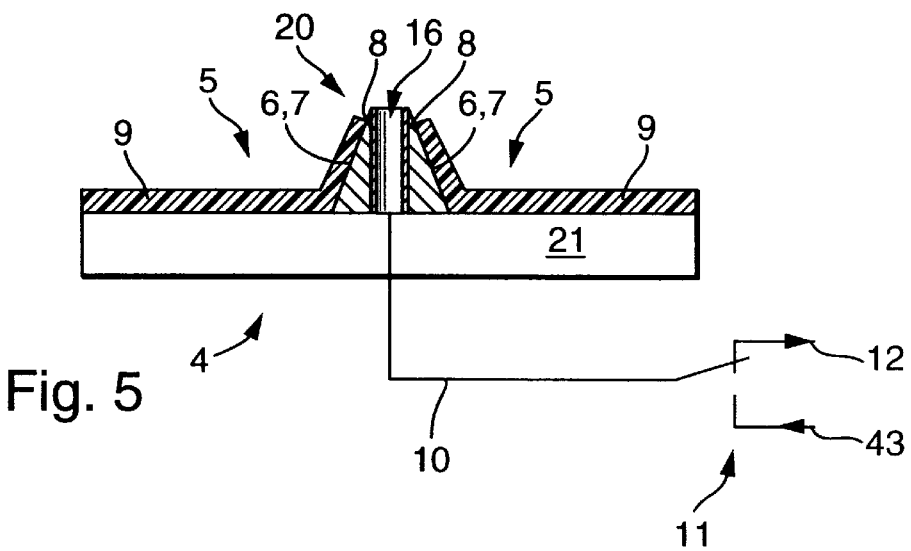
FIG. 5 is a representation similar to FIG. 1, where, however, the electrode is constructed as a hollow electrode in the shape of a truncated cone with cylindrical inner cavity.
Figure 6:
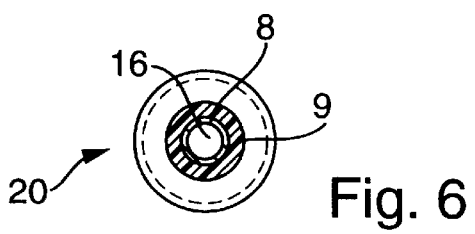
FIG. 6 is a plan view of the electrode according to FIG. 5.
Figure 7:
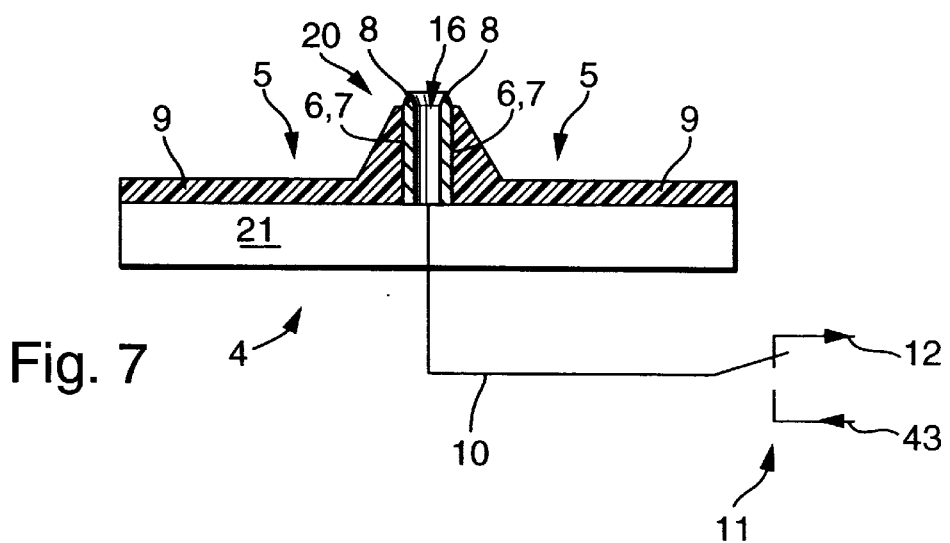
FIG. 7 is a representation similar to FIG. 5, where, however, the electrode has an essentially cylindrical shape.
Figure 8:
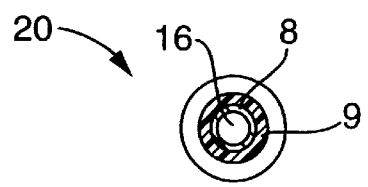
FIG. 8 is a plan view of the electrode according to FIG. 7.

In the embodiments according to FIGS. 5 and 8, the electrode is a hollow electrode, which is installed with its active electrode area 8 projecting beyond the surface of the support area 5 in the surface of the specimen slide 4. The electrode 6,7 according to FIG. 5 is essentially in the shape of a truncated cone and the electrode 6,7 according to FIG. 7 is essentially constructed as a cylindrical sheath, wherein the axis of symmetry of the electrode 6,7 is arranged respectively approximately perpendicular to the surface plane of the specimen slide 4 in the support area 5. The hollow electrode has an inner cavity 16 filled with the nutrient medium 2, which has an opening on the surface of the support area 5. Through this opening, when the electrode 6,7 is arranged in the cell membrane opening, electrically charged particles from the cell liquid can reach into the inner cavity 16 and come into contact with the inner wall of the electrode 6,7 bordering the inner cavity 16. In contrast to the embodiment of FIG. 1, a larger active measuring electrode surface results, such that the electrical contact resistance between the electrode 6,7 and the cell liquid is reduced.

As can be recognized especially well from FIGS. 5 and 7, the open end of the electrode 6,7 bordering the opening has a sharp ring edge, the cross section of which is constructed as a tip and tapers away from the surface plane of the specimen slide to the point on the electrode 6,7 projecting furthest away. During the application of an electric voltage on the electroporation electrode 6,7 in the active electrode area 8, a comparatively high field strength thereby results, which makes the opening of the cell membrane easier.

Figure 3:
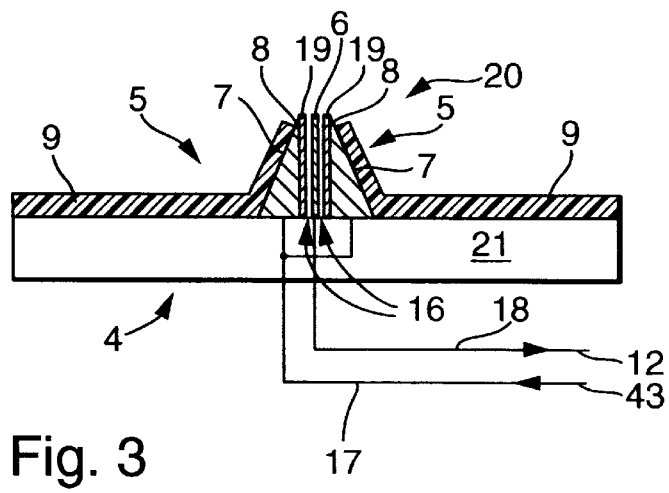
FIG. 3 is a representation similar to FIG. 1, where, however, separate electrodes are provided for the measurement and the electroporation.
Figure 4:
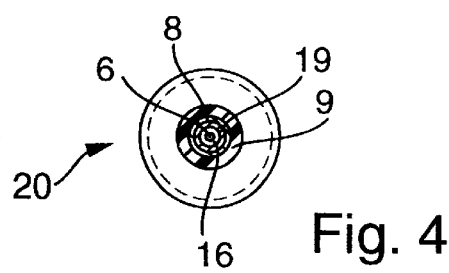
FIG. 4 is a plan view of the measuring and electroporation electrodes according to FIG. 3.

In the embodiment according to FIGS. 3 and 4, a measuring electrode 6 and an electroporation electrode 7 separated from it are arranged in the support area 5 of the specimen slide 4. The electroporation electrode 7 is connected to an electroporation voltage source 43 via a conductor path 17 integrated in the specimen slide 4, for making an opening in the cell membrane of a cell that adheres to the support area 5. An additional conductor path 18 connects the measuring electrode 6 to the input of a measurement amplifier 12. Otherwise, the structure corresponds for the most part to the specimen slide according to FIG. 5. The electroporation electrode 7 has approximately the shape of a truncated cone, and has a cylindrical inner cavity, the cylinder axis of which approximately corresponds with the axis of symmetry of the truncated cone. On the free end of the electroporation electrode 7, the inner cavity has an opening that leads to the surface of the specimen slide 4. The measuring electrode 6 is constructed as a rod electrode which is arranged approximately concentrically in the inner cavity of the electroporation electrode 7 and with its free end extends up to the opening of the inner cavity. In order to uncouple the measuring electrode 6 from the parasitic capacitiance of the electroporation electrode 7 and its supply line, and to increase the electric resistance between the measuring electrode 6 and the electroporation electrode 7, an insulator layer 19 can be arranged on the inner wall of the electroporation electrode 7 which delimits the inner cavity 16. The insulator layer 19 electrically insulates the cell liquid located in the inner cavity 16 from the electroporation electrode 7.

It should also be mentioned that the measuring electrode 6 and/or the wall that delimits the inner cavity 16 of the measuring and electroporation electrode(s) 6,7 can have a surface roughness which enlarges the surface of the electrode. The electrode(s) 6,7 can, for example, consist of porous silicon or a coating made of this material.

As can be recognized especially well from FIGS. 1 to 10, the electric insulator 9 has within the support area 5 a projection 20 that projects beyond its surface plane, on which projection is arranged the free end of the active electrode area of the electroporation electrode 7, which faces away from the surface plane. The active electrode area 8 is thus electrically well coupled to the cell 3 that adheres to the support area. The cross section of the projection 20 tapers going away from the surface plane of the support area 5 to the point that projects the furthest outwardly. The projection 20 and the electrode(s) 6,7 can thus be manufactured with better production engineering. Moreover, the tapering projection 20 has a good mechanical rigidity.

The projection 20 can, however, also have a cross section that is constant in its extension direction or decreases going away from the surface plane of the support area 5 to the furthest projecting point. Such a projection 20 can, for example, be manufactured using LIGA-technology.

It should also be mentioned that the specimen slide 4 has a substantially plate-shaped substrate 21 which, for example, can consist of a semiconductor material (e.g. silicon or gallium-arsenide), silicon carbide, glass or plastic. On this substrate the insulator 9 can be applied as a coating, for example by sputtering. Optionally, the substrate 21 can also be a flexible film.

In the embodiment according to FIGS. 11 to 18, the specimen slide 4 has in the support area 5 respectively several profile recesses 22 surrounding the electroporation electrode 7. As can be recognized especially well from FIG. 11, the seal of the cell membrane of the cell 3 against the support area 5 of the specimen slide 4 can be improved by this.

Figure 11:
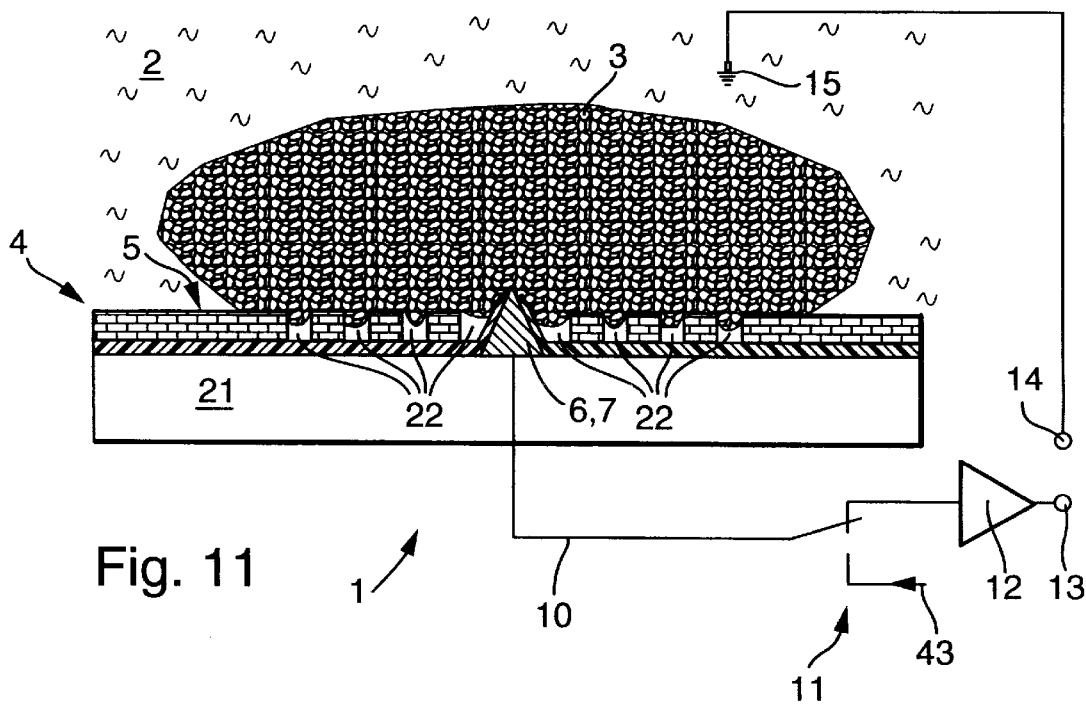
FIG. 11 is a longitudinal section of an apparatus with a specimen slide having an electrode on which is adherently supported a biological cell located in a nutrient medium.
Figure 12:
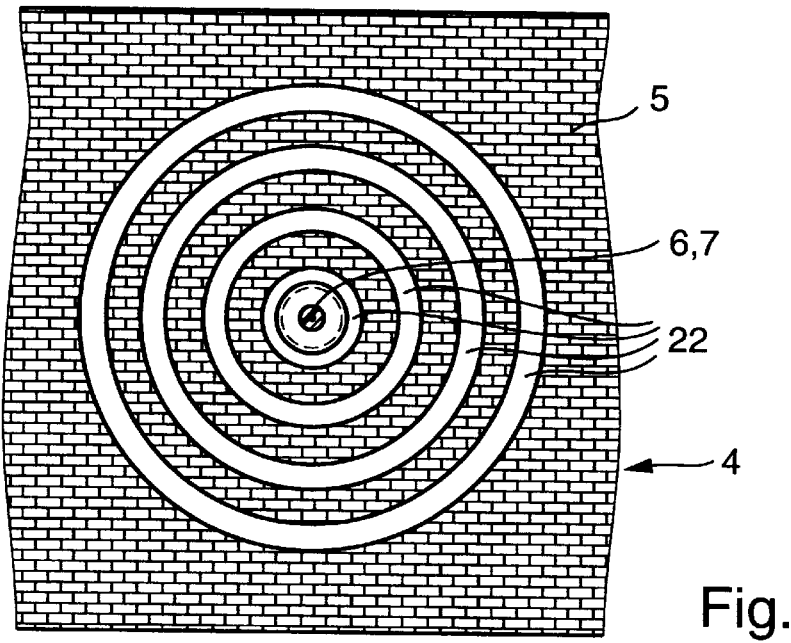
FIG. 12 is a plan view of the specimen slide shown in FIG. 11.

In the embodiment according to FIGS. 11 to 14, the profile recesses are closed ring grooves, which are arranged concentrically to the electroporation electrode 7. The ring grooves each have an approximately rectangular shaped cross section. Ring grooves adjacent to each other are arranged respectively at equal distances from each other (FIG. 12). The distances between adjacent profile recesses 22 and the depth of these profile recesses 22 are adapted to the type of cells 3 to be supported on the support area 5. The edges of the profile recesses 22 can be rounded in order to make the adherent supporting of a cell 3 easier.

Figure 15:
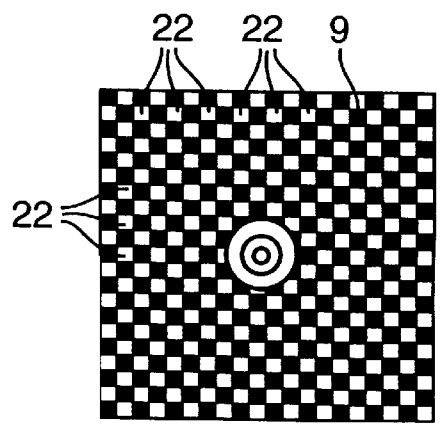
FIGS. 15 and 16 are views similar to FIG. 14, where, however, the specimen slide has another surface profile.
Figure 16:
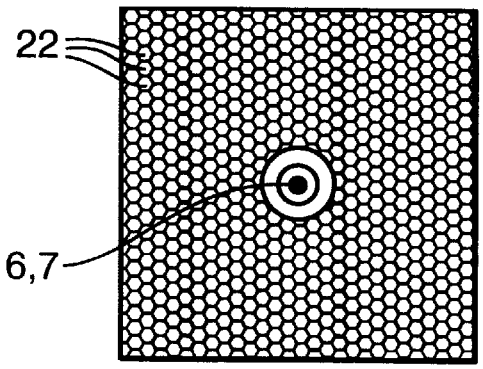

The profile recesses 22 can have gaps in their course, as is shown in the example of a checkerboard structure in FIG. 15 and a honeycomb structure in FIG. 16. The surface profiles according to FIGS. 14 to 16, the surface roughness, and the surface material can be respectively adapted to a certain cellular type. In this way, the cell adhesion can be improved or controlled.

Figure 18:
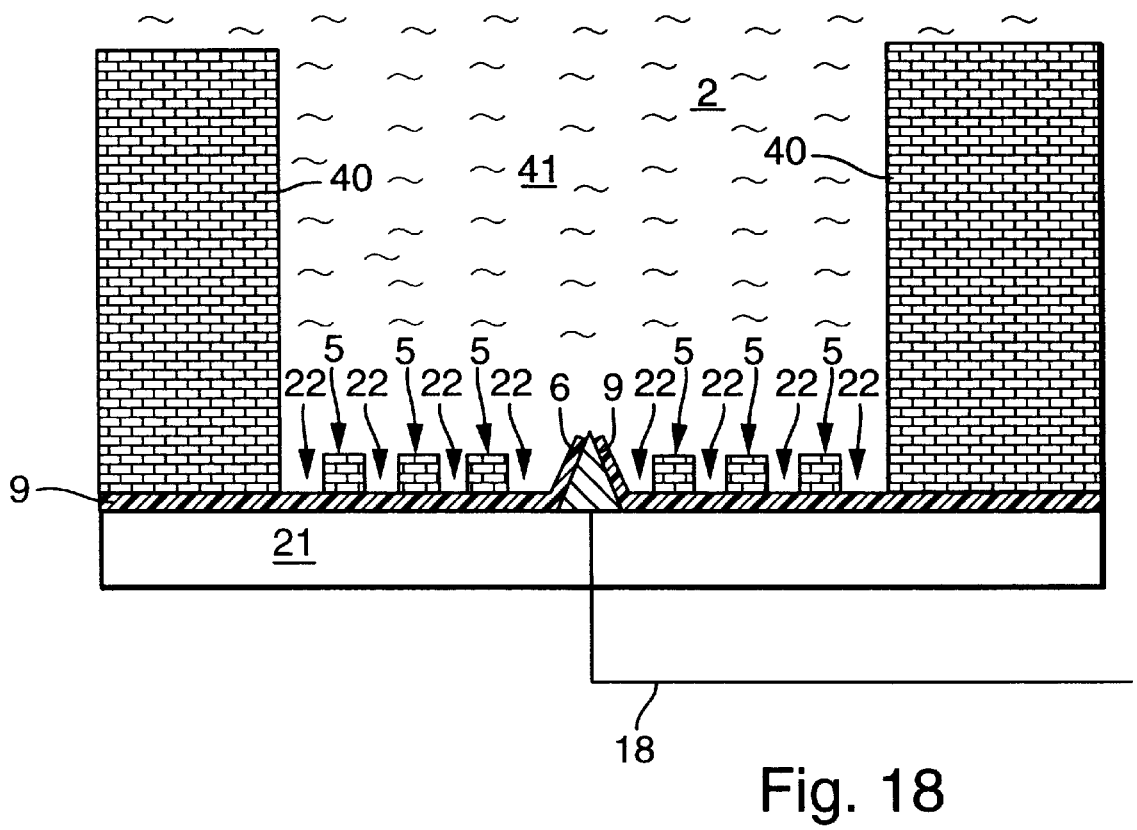
FIG. 18 is a longitudinal section through a specimen slide, which has an electrode arranged between two boundary walls within a surface profile.

In the embodiments according to FIGS. 11 and 18, the surface profile can be applied on the electric insulator 9 as a coating using methods of semiconductor technology. The specimen slide 4 can thus be manufactured in a simple way as a semiconductor chip. The surface profile can, however, also be applied on the insulator 9 with other processes, for example in thick layer technology. In the embodiment according to FIG. 13, the surface profiling is a layer applied on the substrate 21, which is covered by an insulator layer which forms the insulator 9. By this measure, possible creep (leaking) currents, which flow from the electroporation electrode 7 along the surface of the insulator 9 to the nutrient medium 2, can be reduced. A suitably high electric resistance thereby results between the electrode 6,7 and the nutrient medium 2, when a cell 3 is supported on the support area 5.

Figure 13:
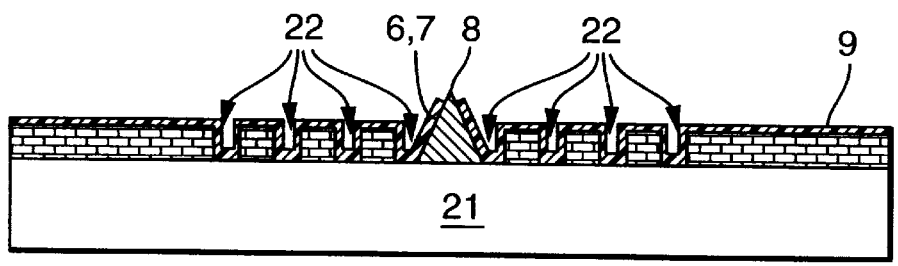
FIG. 13 is a longitudinal section through a specimen slide, which has a surface profile surrounding the electrode, on which an electric insulation layer is mounted.
Figure 14:
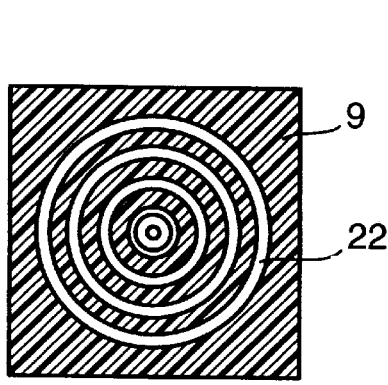
FIG. 14 is a plan view of the specimen slide according to FIG. 13.

The manufacture of the surface profile shown in FIG. 13 can be accomplished, for example, in a manner where on the substrate 21 a ring structure is applied using a mask technique, which is then coated with the insulation layer. The profiling then has, in comparison to the embodiment according to FIG. 11, somewhat more rounded edges. The cells 3 can then be supported better.

In the embodiment according to FIG. 18, boundary walls 40 are arranged on both sides of the electrode, which walls form together with the insulator 9 a guide channel 41 that is somewhat U-shaped in cross-section. In this, the profiles 22 and the measuring electrode on the floor of the guide channel 41 are arranged between the boundary walls 40. The boundary walls 40 form an obstruction for cells 3 located in the guide channel 41, which these cells cannot or not easily surmount. The cells 3 can thus essentially only move in the extension direction of the guide channel 41, where they forcibly come into contact with the measuring electrode 6. The clear spacing of the boundary walls 40 arranged on both sides of the measuring electrode 6 is adapted to the dimensions of the cells 3 and is preferably somewhat larger than the diameter of the cells 3. Optionally, several measuring electrodes 6 can be arranged one behind the other in the extension direction of the guide channel 41. In this way, the cell potential can be measured on several cells 3 at the same time. The cross-section of the guide channel 41 can taper or expand in the extension direction, i.e. the guide channel 41 can have a different width and/or different cross-sectional dimensions at different positions. Starting from the deepest to the widest-projecting point of the guide channel 41, the cross section of the guide channel 41 can taper, for example.

Figure 9:
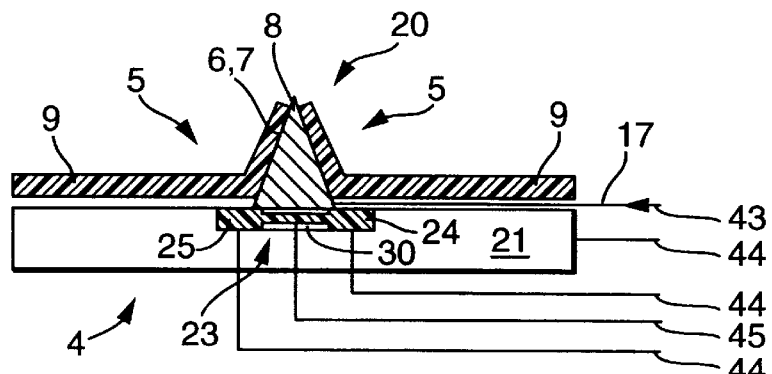
FIG. 9 is a longitudinal section of a device in which the measuring and electroporation electrode is electrically coupled to the gate of a J-FET.

In the embodiment according to FIG. 9, a junction-field effect transistor (J-FET) 23 is integrated into the substrate 21 of the specimen slide 4. Directly above the gate of the J-FET, the measuring and electroporation electrode 6,7 is arranged, which is connected with the gate in a galvanically conducting manner. An additional gate-electrode 30 allows an external control of the channel conductivity, which makes possible an operating point adjustment Source 24 and drain 25 of the J-FET 23 are connected via conductor paths integrated into the specimen slide 4 with an evaluation device. The J-FET 23 has a very low noise, a high input impedance, as well as a low input capacitance, and causes an impedance transformation of the electric signal that is uncoupled from the cell 3. With the J-FET 23, the measuring and electroporation electrode 6,7 is for the most part uncoupled from the conducting capacitance of the conductor paths connected to the source 24 and the gate 25. In this way, high-frequency signal portions of the cell potential signal can be better measured.

For the electroporation of the cell membrane, the electroporation electrode 7 can be connected with a conductor path 17 integrated in the specimen slide 4 to an electroporation voltage source 43. Instead of coupling the electroporation voltage via the conductor path 17, the electroporation voltage can also be coupled capacitively via the gate of the J-FET 23 into the electrode 6,7, in which case the conductor paths 44 connected to the source 24 and the drain 25, and possibly the substrate 21, are connected to the electroporation voltage source. In this case, the conductor path 17 can be omitted.

Figure 10:
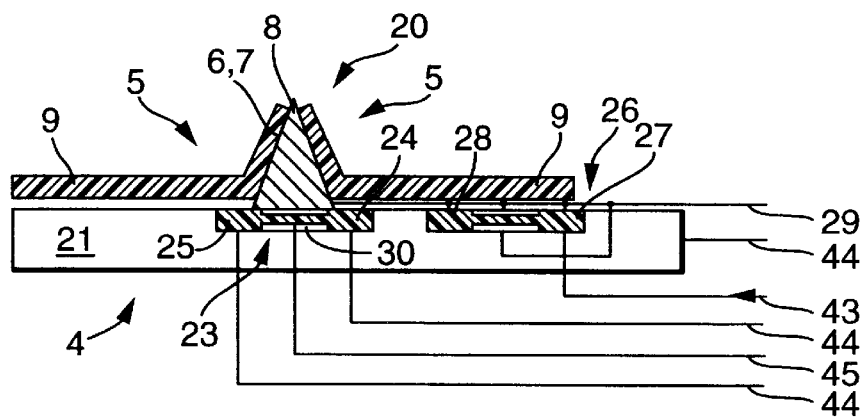
FIG. 10 is a representation similar to FIG. 9, where, however, adjacent to the electrode, an additional field effect transistor is arranged functioning as a switch, by which the electrode can be connected to an electroporation voltage source.

In the embodiment according to FIG. 10, a switch-FET 26 is integrated into the specimen slide 4 in close proximity to the J-FET 23. The drain connection 27 of this switch-FET 26 is connected to the electroporation voltage source 43 and the source connection 28 to the electrode 6,7. To apply the electroporation voltage to the electrode 6,7, the gate of the switch-FET 26 is connected to a control line 29, onto which a control voltage is applied. In an advantageous way, the electrode 6,7 is to the greatest extent uncoupled from leaking capacitance and couplings of the connection line to the electroporation voltage source by the blocked source-drain connection.

Figure 17:
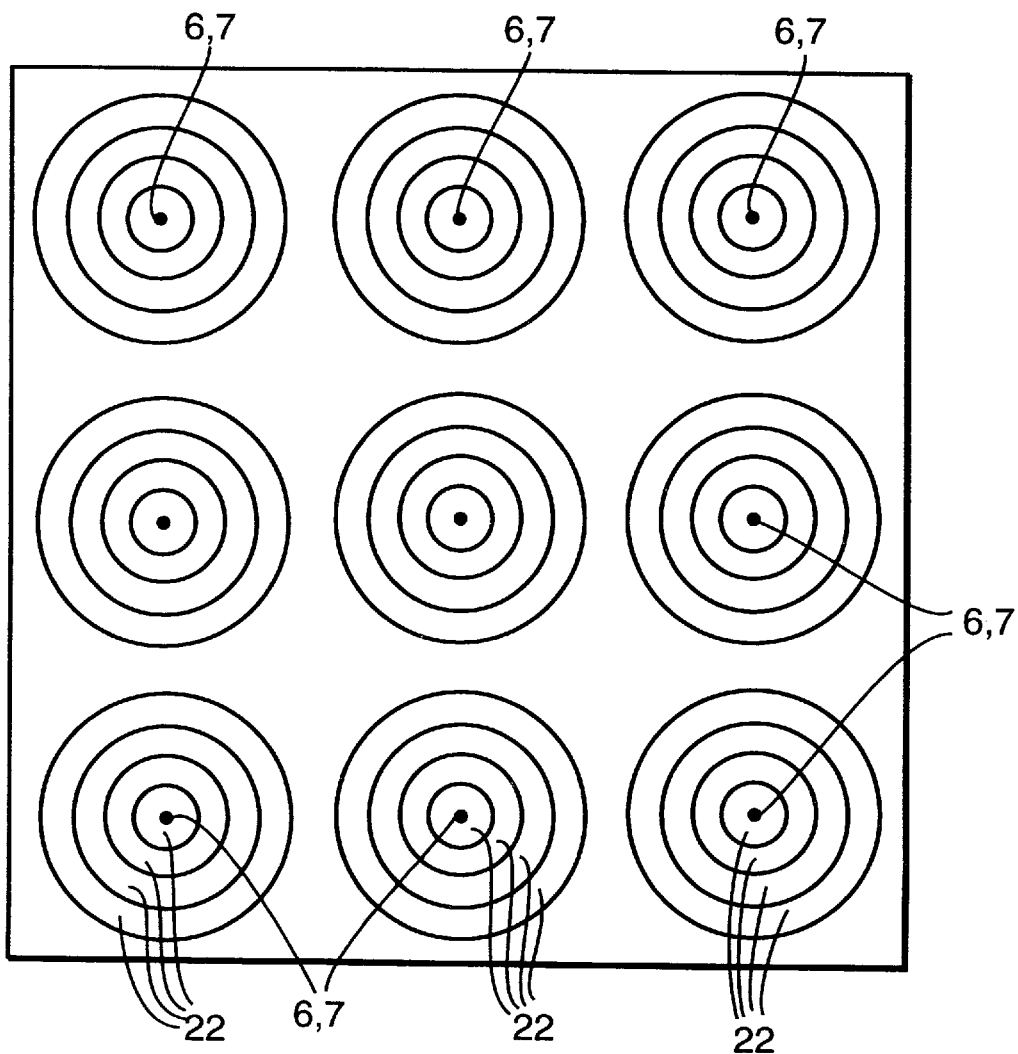
FIG. 17 is a plan view of a specimen slide that has an array with several measuring and electroporation electrodes.

In the embodiment according to FIG. 17, in the support area 5 of the specimen slide 4, several measuring and electroporation electrodes 6,7 are arranged in the form of an array. The individual electrodes 6,7 are respectively arranged at grid points of a Cartesian coordinate system. In this way, a locationally triggered measurement of the electric signal of a cell population supported on the support area 5 is possible. The electrodes 6,7 can also be distributed in other ways in the support area 5, for example in rows or columns set apart from each other or randomly distributed.

On and between the electrodes 6,7, in order to optimize the growth rate of the cells 3, conductive structures can be arranged, which also makes possible a targeted supporting of cells 3 and/or between the electrodes 6,7. The conducting structures can, for example, contain a surface structuring, a coating or a suitable topography formation. For different cell types or measuring tasks, different distances between adjacent active electrode areas 8 can be provided.

On the whole, a method thus results for measuring the cell potential of a biological cell 3, in which the cell in a nutrient medium 2 is supported adhering to a support area 5. Within the support area 5 of the cell 3, at a distance from the support edge, an opening is made in the membrane of the cell 3. In the process, the edge of the cell membrane, that adheres to the support area 5 and borders the opening, seals the cell liquid located inside the cell 3 against the nutrient medium 2. Through the opening, the electric voltage is measured between the cell liquid and the nutrient medium 2.

Figure 19:
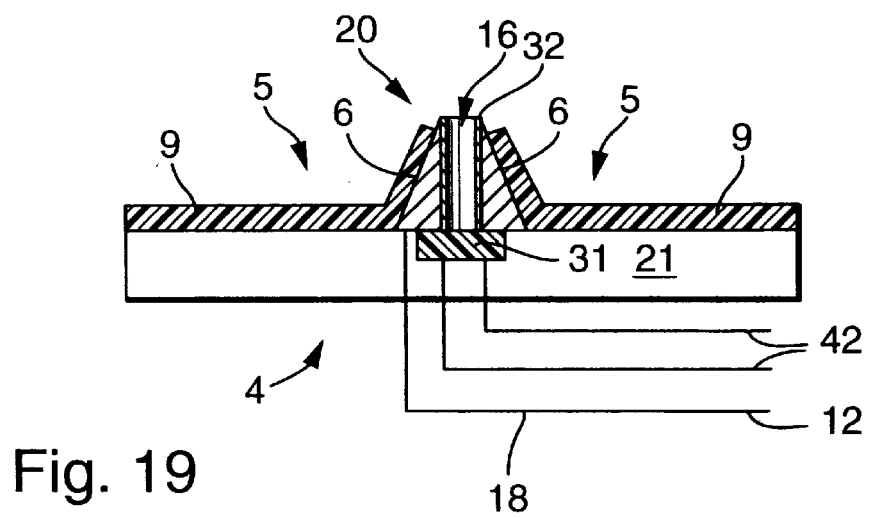
FIG. 19 is a longitudinal section through a measuring and electroporation electrode that can be moved using a piezo element and is arranged in the support area of a specimen slide.

In the embodiment according to FIG. 19, a piezo element 31 is arranged between the measuring electrode 6 and the specimen slide 4. The piezo element carries the measuring electrode 6 on its free end, that can be moved relative to the specimen slide 4, and is affixed on the substrate 21 of the specimen slide 4 by its end facing away from the free end. As in the embodiment according to FIGS. 5 and 6, the measuring electrode 6 is constructed approximately in a truncated cone shape and has an essentially cylindrical inner cavity 16 that extends along the axis of the truncated cone. This inner cavity 16 has on the free end of the measuring electrode facing away from the piezo element 31 a circular opening which is bordered by a ring-shaped electrode area, which has a sharp edge 32 facing away from the support area 5. Using the piezo element 31, the edge 32 of the measuring electrode 6 can be moved relative to the specimen slide 4 toward and away from a cell 3 that is supported on the support area 5. In this way, an approximately circular disc-shaped area of the cell membrane is cut out of the membrane structure of the cell 3, so that cell liquid located inside of the cell 3 can pass through the resulting opening to come into contact with the measuring electrode 6. The inner cavity 16 of the measuring electrode 6 is filled with an electrolyte by which ions contained in the cell liquid can proceed to the inner walls of the measuring electrode 6 bordering the inner cavity 16, after the opening is made in the cell membrane. In this way, a good electrical contact between the cell liquid and the measuring electrode 6 is made.

In the support area 5 an electric insulator surrounding the measuring electrode 6 is arranged, which insulator is brought via the cone envelope surface of the measuring electrode 6 right up to the sharp edge 32. The cell 3 supported on the support area 5 adheres by its cell membrane to the insulator 9, whereby the edge of the cell membrane surrounding the opening made in the cell membrane seals off the cell liquid located inside the cell 3 from the nutrient medium 2 in an electrically insulating manner. To measure the cell potential, the measuring electrode 6 is connected via a conductor path 18 integrated in the specimen slide 4 to a measurement amplifier 12. A reference electrode 15 (as shown in FIG. 11, but not shown in FIG. 19) located in contact with the nutrient medium 2 functions for determining a reference potential. The conductor path 18 and the insulator 9 consist of an elastic material which allows a relative movement between the measuring electrode 6 and the substrate 21 of the specimen slide 4 upon a triggering of the piezo element via the control lines 42.

Figure 20:
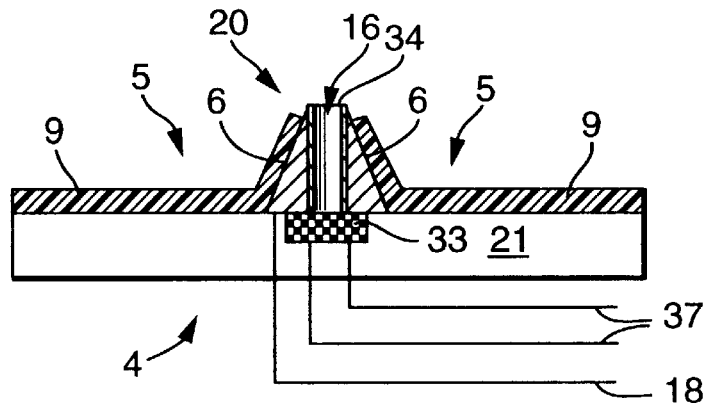
FIG. 20 is a longitudinal section through an electroporation electrode that has an optical window and is arranged in the support area of a specimen slide, behind which a laser diode is arranged.

In the embodiment according to FIG. 20, a laser diode 33 is provided for making a hole in the cell membrane of a cell 3 supported on the support area 5. The laser diode is arranged, as observed from the support area 5, behind an optical window 34 provided in the measuring electrode 6 and integrated into the substrate 21. The laser diode 33 is connected using connection lines 37 to a power supply and control device (not shown). The optical window 34 is constructed as a through-passage hole, which penetrates the measuring electrode 6 approximately in a direction normal to the surface of the support area 5. Using the laser diode 33, a portion of the cell membrane of the biological cell 3, supported on the support area 5 and the measuring electrode 6, can be irradiated with a laser beam, which absorbs the cell membrane of the cell 3. In this way, an opening is made in the cell membrane. After making the opening, the laser beam is turned off, so that then the cell potential can be measured through the opening using the measuring electrode 6. As in the embodiment according to FIG. 19, the cell 3 adhering to the insulator 9 bordering the measuring electrode 6 seals the measuring electrode 6 off against the nutrient medium 2.

Figure 21:
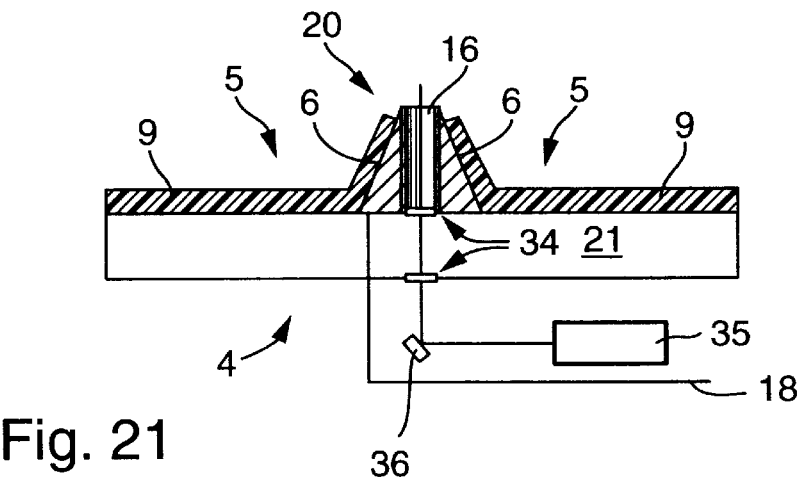
FIG. 21 is a representation similar to FIG. 20, where, however, an external laser is used, which has a laser beam that is coupled into the optical window.

In the embodiment according to FIG. 21, an external laser 35 is provided for making the opening in the cell 3 that adheres to the support area 5. The laser 35 has a beam that can be coupled to the rear side of the specimen slide 4 facing away from the measuring electrode 6, for example using a beam guide device 36 which can include an optical light guide and/or a deflection mirror as well as possibly a focusing device. The beam passes through an optical window provided in the substrate 21 and into the hole in the cell 3 that is penetrated by the measuring electrode 6.

Figure 22:
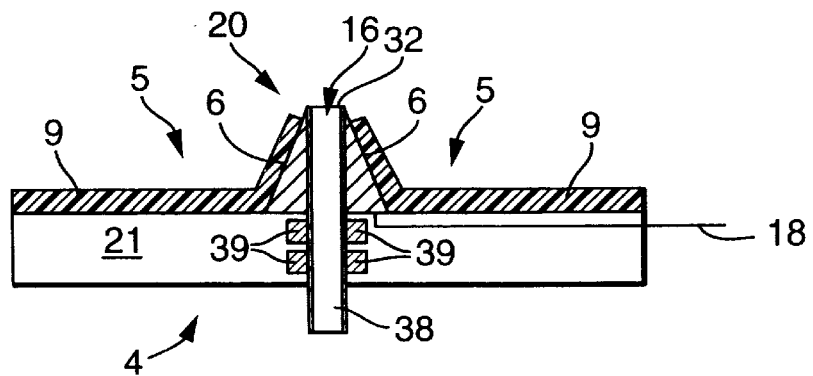
FIG. 22 is a representation similar to FIG. 5, where, however, through the electrode a liquid channel leads to the support area and where several measuring probes are arranged in the course of the liquid channel.

In the embodiment according to FIG. 22, the inner cavity 16 of the measuring electrode 6 is connected to a liquid channel 38, which can be impinged by a controllable partial vacuum. The liquid channel 38 can, for this purpose, be connected to a micropump, for example, by which the nutrient medium 2 can be sucked out from the support area 5 of the specimen slide 4. In this way, the mounting of a cell 3 on the measuring electrode 6 is made easier. Optionally, after the supporting on the measuring electrode 6 of a cell that is suctioned via the liquid channel 38, a weak partial vacuum can be exerted on the cell 3 for a certain time period, until it automatically adheres to the support area 5.

As in the embodiment according to FIG. 19, the edge of the measuring electrode 6 surrounding the opening of the inner cavity 16 has a ring-shaped sharp edge 32, which projects beyond the surface plane of the support area 5. After supporting the cell 3 on the measuring electrode 6, a portion of the cell membrane is impinged by a partial vacuum for a short time, by suctioning off nutrient medium 2 at the liquid channel 38, to such an extent that the membrane area bordered by the sharp edge 32 of the measuring electrode 6 is detached from the membrane structure. In this way, an opening is made in the cell membrane, through which the measuring electrode 6 can come into contact with the cell liquid located inside the cell 3. After making the opening, the partial vacuum is switched off in the liquid channel 38. Optionally, after making the opening, a small quantity of cell liquid can be suctioned into the liquid channel 38 so that it comes into contact with microsensors 39 arranged in the liquid channel 38 adjacent to the measuring electrode 6. In this way, additional cell parameters, for example the gas content and/or an ion concentration of the cell liquid, can be measured.

After making the opening in the membrane of the cell 3, the transport direction of the micropump connected to the liquid channel 38 can be reversed for a short time, in order to inject a substance found in the liquid channel 38, for example a medication and/or a fluorescent coloring agent, through the opening of the cell membrane directly into the cell interior. If no cell 3 is supported on the electrode 6, the liquid channel 38 can nevertheless be used in order to add an appropriate substance to the nutrient medium 2.

In the embodiment according to FIG. 18, in an approximately ringshaped area around the free end of the measuring electrode 6 constructed as a sharp tip and projecting beyond the surface plane of the support area 5, a chemical substance is immobilized which, upon contact with a cell 3 supported in the support area 5, makes an opening in the membrane of the cell 3 . Through this opening, the tip of the measuring electrode 6 can come into contact with the liquid of the cell 3. The apparatus 1 has a particularly simple construction.

It will be appreciated by those skilled in the art that changes could be made to the embodiment(s) described above without departing from the broad inventive concept thereof. It is understood, therefore, that this invention is not limited to the particular embodiment(s) disclosed, but it is intended to cover modifications within the spirit and scope of the present invention as defined by the appended claims.

We claim:

1. An apparatus for measuring a state variable of at least one biological cell (3) located in a nutrient medium (2), comprising a specimen slide (4) having a support area (5) or which the cell (3) is supportable in an adherent manner, at least one measuring probe for contact with a liquid located inside the cell (3) for measuring the state variable, and a measurement amplifier 12 allocated to the measuring probe, wherein the measuring probe is arranged within the support area (5) with an electric insulator (9) surrounding it, such that the cell (3) is supportable on the insulator (9) to seal it from the nutrient medium (2), and at least one poration tool is arranged in the support area (5) tor forming an opening in a membrane of the cell (3), said opening being in an area of the measuring probe.

2. The apparatus according to claim 1, wherein the poration tool is arranged substantially concentrically around the measuring probe.

3. The apparatus according to claim 1, wherein the measuring probe comprises a measuring electrode (6), to which is allocated at least one reference electrode (15) contactable with the nutrient medium (2) for measuring a potential of the cell (3).

4. The apparatus according to claim 3, wherein the measuring electrode (6) includes an electroporation electrode (7) connectable to an electric voltage source for electroporation of the cell membrane, and the electroporation electrode (6,7) has at least one active electrode area (8) arranged within the support area (5) and surrounded by the electric insulator (9).

5. The apparatus according to claim 1, wherein the poration tool comprises an electroporation electrode (7) spaced from the measuring probe, the electroporation electrode being connectable to an electric voltage source for electroporation of the cell membrane, the electroporation electrode (7) having at least one active electrode area (8) arranged within the support area (5) and surrounded by the electric insulator (9).

6. The apparatus according to claim 4, wherein the active electrode area (8) of the electroporation electrode (6,7) has at least one sharp tip and is arranged to project beyond a surface plane of the support area (5).

7. The apparatus according to claim 4, wherein the electroporation electrode (7) comprises a hollow electrode having an inner cavity (16) with an opening located on a surface of the support area (5), and the measuring electrode (6) comprises a rod electrode arranged in the inner cavity (16) of the electroporation electrode (7), a free end of the rod electrode extending up to the opening of the inner cavity (16).

8. The apparatus according to claim 4, further comprising a static switching element arranged immediately adjacent to the electroporation-electrode (7) for connecting the electroporation electrode (7) to an electroporation voltage source.

9. The apparatus according to claim 4, further comprising at least one actuator for moving the poration tool across the surface of the support area (5) relative to the specimen slide (4), the actuator comprising a piezo element (31).

10. The apparatus according to claim 9, wherein the poration tool has at least one sharp tip (32) contactable with the cell membrane.

11. The apparatus according to claim 9, wherein the actuator is connected to a control device for generating an ultrasonic vibration.

12. The apparatus according to claim 9, wherein the measuring probe is simultaneously also the poration tool and is movable across the surface of the support area (5) relative to the specimen slide (4) using the piezo element (31).

13. The apparatus according to claim 1, wherein the specimen slide (4) has an optical window (34) in an area of the measuring probe, the window being arranged in a beam path of a laser beam in order to open the cell membrane.

14. The apparatus according to claim 13, further comprising a laser diode integrated into the specimen slide (4) to generate the laser beam.

15. The apparatus according to claim 13, wherein the measuring probe is arranged substantially concentrically around the optical window (34).

16. The apparatus according to claim 1, wherein the poration tool comprises one of a chemical substance and at least one outlet opening connected to a supply channel for a chemical substance for opening the cell membrane.

17. The apparatus according to claim 1, wherein the poration tool has at least one channel opening into the support area (5) for admitting a partial vacuum or excess pressure to impinge upon a portion of the cell membrane to form the opening in the cell membrane.

18. The apparatus according to claim 1, wherein the measuring probe comprises a hollow sensor (16) installed in a surface of the specimen slide (4) and having at least one inner cavity (16), wherein the inner cavity (16) has an opening on the surface of the support area (5).

19. The apparatus according to claim 1, wherein the electric insulator (9) within the support area (5) has a projection (20) that projects beyond a surface plane of the support area (5), and the measuring probe is arranged on a free end of the projection (20) facing away from the surface of the support area (5).

20. The apparatus according to claim 19, wherein a cross-section of the projection (20) tapers from the surface plane of the support area (5) to a point furthest from the plane.

21. The apparatus according to claim 1, wherein the specimen slide (4) has a profile in the support area (5), the profile having at least one profile recess (22) and/or projection surrounding the measuring probe.

22. The apparatus according to claim 21, wherein the profile recess (22) and/or projection is interrupted in its extension direction by at least one gap.

23. The apparatus according to claim 21, wherein the profile recess (22) and/or projection has a ring-shape, and a plurality of ring-shaped profile recesses (22) and/or projections are arranged substantially concentrically to the measuring probe.

24. The apparatus according to claim 21, wherein the insulator (9) is an insulation layer arranged on a surface of the profile.

25. The apparatus according to claim 21, wherein a profile projection(s) is (are) mounted on a surface of the insulator (9).

26. The apparatus according to claim 1, further comprising at least one coating arranged in the support area (5) of the specimen slide (4) and applied on its surface, the coating being selected from the group consisting of a cell adhesion protein, a hydrophilic coating, and a hydrophobic coating immediately adjacent to the measuring probe.

27. The apparatus according to claim 1, further comprising boundary walls arranged on both sides of the measuring probe as a mechanical guide for the cells (3), the boundary walls delimiting a groove-shaped guide channel (41).

28. The apparatus according to claim 1, further comprising a field effect transistor (FET) (23) arranged adjacent to the measuring probe (6), wherein the measuring probe is connected to a gate of the FET (23) for impedance transformation of a measurement signal.

29. The apparatus according to claim 1, further comprising at least one liquid channel (38) opening in the support area (5) of the specimen slide (4), the channel being surrounded by the measuring probe.

30. The apparatus according to claim 29, wherein at least one micropump is integrated in the specimen slide (4) in the course of the liquid channel (38).

31. The apparatus according to claim 30, further comprising at least one microsensor (39) arranged within a wall of the liquid channel (38) for measuring a quantity of the cell (3).

32. The apparatus according to claim 1, further comprising at least one additional electrode arranged in or adjacent to the support area (5) to generate an electric field connecting the cell (3) to the measuring probe.

33. The apparatus according to claim 1, wherein several measuring probes are arranged as an array in the support area and to each of these measuring probes at least one poration tool is allocated.

* * * * *